United States Patent [19]

Schwabe et al.

[11] Patent Number: 4,965,295
[45] Date of Patent: Oct. 23, 1990

[54] DIMENSIONALLY STABLE IMPRESSION COMPOSITIONS

[75] Inventors: Peter Schwabe; Ottfried Schlak; Gottfried Knispel; Reiner Voigt, all of Leverkusen, Fed. Rep. of Germany

[73] Assignee: Bayer Aktiengesellschaft, Leverkusen, Fed. Rep. of Germany

[21] Appl. No.: 338,358

[22] Filed: Apr. 12, 1989

Related U.S. Application Data

[63] Continuation of Ser. No. 94,962, Sep. 19, 1987, abandoned, which is a continuation of Ser. No. 713,058, Mar. 18, 1985, abandoned.

[30] Foreign Application Priority Data

Mar. 23, 1984 [DE] Fed. Rep. of Germany ....... 3410646

[51] Int. Cl.$^5$ ................................................. A61K 6/10
[52] U.S. Cl. ..................................... 523/109; 523/120; 524/862; 528/31; 264/19
[58] Field of Search ................ 523/109, 120; 524/862; 528/31; 264/19

[56] References Cited

U.S. PATENT DOCUMENTS

| | | | |
|---|---|---|---|
| 2,709,161 | 5/1955 | Kilbourne, Jr. et al. | |
| 4,035,453 | 7/1977 | Hittmair et al. | 528/31 |
| 4,222,983 | 9/1980 | August et al. | 524/862 |
| 4,273,902 | 6/1981 | Tomioka et al. | 528/31 |
| 4,356,116 | 10/1982 | Beers | 525/477 |
| 4,356,116 | 10/1982 | Beers . | |
| 4,430,461 | 2/1984 | Deering et al. . | |

FOREIGN PATENT DOCUMENTS 2926405  1/1980  Fed. Rep. of Germany .
2400052  3/1979  France .

Primary Examiner—Melvyn I. Marquis
Attorney, Agent, or Firm—Sprung Horn Kramer & Woods

[57] ABSTRACT

In a silicone impression and duplicating composition which undergoes crosslinking at ambient temperature by an addition reaction, comprising (a) an organopolysiloxane possessing two or more vinyl groups in the molecule, (b) optionally an organopolysiloxane without reactive groups, (c) an organopolysiloxane possessing two or more Si-H groups in the molecule, (d) a catalyst, (e) a filler and, (f) optionally an auxiliary and/or colorant, the improvement wherein polysiloxane components (a)-(c) contain not more than about 1.5% by weight of volatile oligomers, whereby the dimensional stability of impressions is improved.

7 Claims, No Drawings

DIMENSIONALLY STABLE IMPRESSION COMPOSITIONS

This application is a continuation of application Ser. No. 094,962, filed Sep. 9, 1987, now abandoned, which is a continuation of Ser. No. 06/713,058, filed Mar. 18, 1985, now abandoned.

The present invention relates to dimensionally stable impression compositions or duplicating compositions which are based on polysiloxane and are used in particular in the dental sector.

The present invention relates in particular to vinylsilicone pastes which crosslink by an addition reaction and are used for the preparation of exact impressions of toothed, partially toothed and toothless jaws and of plaster models. This is a room temperature vulcanizing two-component silicone rubber system, in which the basic paste containing the crosslinking agent is mixed with a catalyst paste and undergoes crosslinking at room temperature.

Systems of this type are known per se (see, for example, R. G. Craig, Restorative Dental Materials, The C. V. Mosby-Comp., St. Louis, 1980, page 195 et seq.).

In dental engineering, such molding compositions are employed for the production of plaster models and for the replication of these plaster models. Most commonly used duplicating compositions are those based on agaragar, although these have the disadvantage that they require exact temperature control and are therefore slow to process further. Such compositions result in the impression having a restricted shelf life, because the water evaporates slowly.

In the impression compositions sector, the silicone pastes are widely used. In general, they consist of a silicone oil which is mixed with fillers and is based on polydimethylsiloxane possessing terminal hydroxyl groups—which is applied by a variety of methods and is therefore available in various consistencies—and a liquid or pasty curing component which contains a metal salt of a (mono)carboxylic acid, as a catalyst, and a silicic acid ester as a crosslinking agent (see, for example, W. Noll, Chemie u. Technologie der Silicone (Chemistry and Technology of the Silicones), Verlag Chemie, Weinheim, 2nd edition 1964, pages 339(40).

The two components of the silicone system are mixed before use and then undergo crosslinking at roomtemperature in the course of 2-5 minutes as a result of a polycondensation reaction. This gives not only the crosslinked silicone rubber, but also small amounts of alcohol, which slowly diffuse out of the rubber and cause linear shrinkage. This leads to a change in dimensions, and hence to inexactness, in the impression.

In the case of the vinylsilicone impressions which have been known for some years and which undergo crosslinking by a polyaddition reaction, the shrinkage is substantially lower. These compositions consist of a basic paste, containing a silicone oil, a filler and a crosslinking agent, and a catalyst paste containing a silicone oil, a filler and a catalyst.

The silicone oil is predominantly a polydimethylsiloxane possessing terminal vinyl groups, the cross-linking agent contains reactive SiH groups, and the catalyst consists of platinum or a platinum complex. In this system, apart from the model exhibiting relatively high dimensional precision, the basic paste and catalyst paste are easier to meter because they have the same viscosity and the mixing ratio of the two pastes has been adjusted to 1:1, and the pastes are completely tasteless and odorless.

The starting substance, such as silicone oils containing vinyl groups, polydimethylsiloxanes possessing terminal trimethylsiloxy groups, and polysiloxanes containing SiH groups (crosslinking substances), are prepared in a manner which is known per se (see, for example, W. Noll, loc. cit. pages 162-206).

If the content of volatile oligomers in these starting materials is determined by standard methods (for example by DIN 51,581), it is found, as a rule, that the weight loss is about 1 to 2% by weight. If such raw materials are used to produce impression compositions or duplicating compositions, unsatisfactory results are obtained. If, for example, the change in dimensions is measured (according to ADA Specification No. 19 after 24 hours, a linear shrinkage of 0.25-0.45% is found, depending on the filler content of these pastes. These values are lower than those of the impression compositions based on silicones which undergo crosslinking by a condensation reaction, the values for these being 0.5-0.9%. Nevertheless, the values should be below 0.2% in order to ensure optimum accuracy of fit of the future tooth replacement.

Surprisingly, it has now been found that it is possible to obtain these values if, in accordance with the invention, the liquid components in the compositions, such as the polydimethylsiloxanes possessing terminal vinyl groups and terminal trimethyl groups and the crosslinking agents containing SiH groups are thoroughly heated by customary methods, for example by means of a thin-film evaporator or a falling-film evaporator, so that, according to the above standard method, they contain less than 1.5 per cent by weight, preferably 0-0.8% by weight, of volatile oligomers.

The present invention thus relates to dimensionally stable impression compositions and duplicating compositions which undergo crosslinking at ambient temperature by an addition reaction, are based on polysiloxane and contain (a) organopolysiloxanes having two or more vinyl groups in the molecule, (b) if appropriate, organopolysiloxanes without reactive groups, (c) organohydrogenopolysiloxanes having two or more Si-H groups in the molecule, (d) a catalyst and (e) fillers and, if appropriate, other customary additives, auxiliaries and colorants, which are characterized in that the liquid polysiloxane components (a)-(c) contain not more than 1.5% by weight of volatile oligomers.

On the other hand, when used for the preparation of exact impressions of toothed, partially toothed and toothless jaws, the vinylsilicone pastes according to the invention are distinguished by their small dimensional change of 0.2% after storage for 24 hours at 23° C., measured according to ADA Specification No. 19. The same low values are also achieved by vinylsilicone pastes according to the invention which are used for the duplication of plaster models.

The following materials are suitable starting materials for the subject of the present invention:

The silicone oil (a) is a polydimethylsiloxane which possesses unsaturated hydrocarbon groups, preferably vinyl groups, on at least two silicon atoms and can have a viscosity in the range from 500 to 200,000 mPa.s at 20°

C., depending on the desired viscosity of the formulated pastes.

According to the invention, the content of volatile oligomers in the vinylsilicone oils is adjusted to not more than 1.5% by weight, preferably 0–0.8% by weight, by passage through a thin-film evaporator.

The silicone oils (b) are polydimethylsiloxanes which possess trimethylsiloxy terminal groups, have a viscosity of 50 to 2000 mPa.s at 20° C. and, according to the invention, contain not more than 1.5% by weight of volatile oligomers after passing through a thin-film evaporator.

These silicone oils containing up to 40% by weight, relative to the total amount of polydimethylsiloxane, preferably serve as plasticizers in the duplicating composition.

The crosslinking agent (c) is a polydimethylsiloxane which has hydrogen atoms on at least two silicon atoms in its molecule and, according to the invention, contains not more than 1.5% by weight of volatile oligomers after passing through a thin-film evaporator.

The catalyst (d) is preferably a platinum complex prepared from hexachloroplatinic (IV) acid. These compounds, too, are known per se. Other platinum compounds which accelerate the addition-crosslinking reaction are also suitable. Examples of very suitable compounds are platinum/siloxane complexes as described in, for example, U.S. Pat. Nos. 3,715,334, 3,775,352 and 3,814,730.

The fillers (e) are understood as meaning ground quartz flors and cristobalite flors, calcium sulphate, calcium carbonate, diatomaceous earth, precipitated and pyrogenically prepared silicon dioxide all with uncoated or coated surfaces.

Colorants are employed to differentiate between the basic paste and the catalyst paste and for monitoring the mixing procedure. Inorganic and organic colored pigments are usually employed.

The examples which follow are intended to illustrate the present invention in more detail.

EXAMPLE 1

(COMPARISON)

The content of volatile oligomers in the polydimethylsiloxanes possessing terminal vinyl and terminal trimethylsiloxy groups and in the crosslinking agents containing SiH groups is determined by means of a standard method, by heating a sample of 200–400 mg thoroughly in a drying pistol at 145° C. and under 20–30 mbar for 45 minutes. In the case of the fillers, the loss on drying is determined after storage at 110° C. for 1 hour.

A basic paste was prepared by mixing, in a kneader, 440 parts of polydimethylsiloxane which possessed terminal vinyl groups, had a viscosity of 10,000 mPa.s at 20° X. and contained 1.9% by weight of volatile oligomers, with 50 parts of polydimethylsiloxane which contained SiH groups, had a viscosity of 50 mPa.s at 20° C. and contained 1.7% by weight of volatile oligomers, 475 parts of very fine quartz flour with a loss on drying of 0.35% by weight, 30 parts of silica which had been pyrogenically prepared and surface-treated and which had a specific surface area of 50 m$^2$/g and a loss on drying of 0.65% by weight, and 5 parts of inorganic colored pigment.

The catalyst paste was prepared by mixing in a kneader, 485 parts of polydimethylsiloxane which possessed terminal vinyl groups, had a viscosity of 10,000 mPa.s at 20° C. and contained 1.9% by weight of volatile oligomers, 485 parts of very fine quartz having a loss on drying of 0.35% by weight, 29.8 parts of silica which had been pyrogenically prepared and surface-treated and had a specific surface area of 50 m$^2$/g and a loss on drying of 0.65% by weight, and 0.2 parts of a platinum/siloxane complex.

EXAMPLE 2

A basic paste and a catalyst paste were prepared according to the data in Example 1, except that the polydimethylsiloxane possessing terminal vinyl groups contained 0.55% by weight of oligomers and the crosslinking agent contained 0.45% by weight of oligomers. As the data in Example 7 show, a dimensionally stable impression composition was obtained.

EXAMPLE 3

(COMPARISON)

A further basic paste was prepared in a kneader by mixing 180 parts of polydimethylsiloxane which possessed terminal vinyl groups, had a viscosity of 10,000 mPa.s at 20° C. and contained 1.9% by weight of oligomers, 300 parts of polydimethylsiloxane which possessed terminal vinyl groups, had a viscosity of 1,000 mPa.s and contained 1.75% by weight of oligomers, 300 parts of polydimethylsiloxane which contains SiH groups, had a viscosity of 95 mPa.s at 20° C. and contained 1.95% by weight of oligomers, 210 parts of precipitated and surface-treated silica having a specific surface area of 90 m$^2$/g and a loss on drying of 1.2% by weight, and 10 parts of an inorganic colored pigment.

A catalyst paste was prepared in a kneader by mixing 78 parts of polydimethylsiloxane which possessed terminal vinyl groups, had a viscosity of 10,000 mPa.s at 20° C. and contained 1.9 % of oligomers, 710 parts of polydimethylsiloxane which possessed terminal vinyl groups, had a viscosity at 1,000 mPa.s at 20° C. and contained 1.75% by weight of oligomers, 210 parts of precipitated and surface-treated silica having a specific surface area of 90 m$^2$/g and a loss on drying of 1.2% by weight, 1.8 parts of an inorganic colored pigment and 0.2 parts of a platinum/siloxane complex.

EXAMPLE 4

A basic paste and a catalyst paste were prepared according to the data in Example 3, by mixing in a kneader. The polydimethylsiloxane possessing terminal vinyl groups and having a viscosity of 10,000 mPa.s contained 0.55% by weight of oligomers, the polydimethylsiloxane possessing terminal vinyl groups and having a viscosity of 1,000 mPa.s contained 0.4% by weight of oligomers, and the crosslinking agent contained 0.45% by weight of oligomers. The data on the dimensional stability are listed after Example 7.

EXAMPLE 5

(COMPARISON)

A basic paste was prepared by mixing, in a kneader, 550 parts of polydimethylsiloxane which possessed terminal vinyl groups, had a viscosity of 10,000 mPa.s at 20° C. and contained 1.9% by weight of oligomers, 200 parts of polydimethylsiloxane which possessed terminal trimethylsilyl groups, had a viscosity of 120 mPa.s and contained 1.65% by weight of oligomers, 200 parts of polydimethylsiloxane which contained SiH groups, had a viscosity of 95 mPa.s at 20° C. and contained 1.95% by weight of oligomers, and 50 parts of precipitated and surface-treated silica having a specific surface area of 90 m²/g and a loss on drying of 1.2% by weight.

The catalyst paste was prepared in a kneader by mixing 540 parts of polydimethylsiloxane which possessed terminal vinyl groups, had a viscosity of 10,000 mPa.s at 20° C. and contained 1.9% by weight of oligomers, 400 parts of polydimethylsiloxane which possessed trimethylsilyl terminal groups, had a viscosity of 120 mPa.s and contained 1.65% by weight of oligomers, 50 parts of precipitated and surface-treated silica having a specific surface area of 90 m²/g and a loss on drying of 1.2% by weight, 9.8 parts of an inorganic colored pigment and 0.2 parts of a platinum,,siloxane complex.

EXAMPLE 6

A basic paste and a catalyst paste were prepared according to the data in Example 5, by mixing in a kneader. The polydimethylsiloxane possessing terminal vinyl groups and having a viscosity of 10,000 mPa.s contained 0.55% by weight of oligomers, the polydimethylsiloxane possessing terminal trimethylsilyl groups and having a viscosity of 125 mPa.s contained 0.25% by weight of oligomers, and the crosslinking agent contained 0.45% by weight of oligomers. As the data in Example 7 show, a dimensionally stable duplicating composition was obtained.

EXAMPLE 7

In accordance with specification No. 19 of the American Dental Association (ADA), a basic paste and a catalyst paste were mixed in a weight ratio of 1:1 (Example 1-4) or 9:1 (Example 5-6) and, 90 seconds after the beginning of mixing, the mixture was introduced onto a block provided with channels and located in a mold. The mold was covered first with a polyethylene film and then with a rigid flat metal plate, and pressed firmly against the mold with application of sufficient force. This assembly was immediately placed in a water bath at a temperature of 32°±1° C. After 7.5 minutes (Example 1-4) or 10 minutes (Example 5-6), the assembly was removed from the water bath, the mold and test block were separated from one another, and the impression was expelled from the mold by means of a lever. The side opposite the reference mark was dusted with talc and, with the impression side facing upwards, transferred to a flat plate which was likewise dusted with talc. The distance between two parallel lines 25 mm apart on the test block provided with lines was measured under a measuring microscope to an accuracy of 0.005 mm and recored as measured value A. 24 hours after the preparation of the impression, the distance between the parallel lines on the impression was measured, and recorded as measured value B. The dimensional change is calculated from $(A-B)/A \times 100$, the mean of 3 determinations being taken.

Results of the measurments of the dimensional change for the impression compositions of Example 1-4 and duplication compositions of Example 5-6 according to ADA Specification 19 were:

| Example | Basic/catalyst paste | Change after 24 hours |
|---|---|---|
| 1 | 1:1 | −0.32% |
| 2 | 1:1 | −0.14% |
| 3 | 1:1 | −0.39% |
| 4 | 1:1 | −0.16% |
| 5 | 9:1 | −0.45% |
| 6 | 9:1 | −0.19% |

It will be understood that the specification and examples are illustrative but not limitative of the present invention and that other embodiments within the spirit and scope of the invention will suggest themselves to those skilled in the art.

We claim:

1. A dimentionally stable silicone impression and duplicating composition which undergoes crosslinking at ambient temperature by an addition reaction, comprising
   (a) a vinyl dimethylsiloxy end blocked dimethylpolysiloxane, which contains vinyl groups on at least two silicon atoms and having a viscosity of 500 to 200,000 mPa.s measured to 20° C.,
   (b) an organopolysiloxane possessing two or more Si-H groups in the molecule,
   (c) a catalyst, and
   (d) a filler,
wherein components (a) and (b) or (a), (b) and a organopolysiloxane without reactive groups contain not more than about 1.5% by weight of volatile oligomers, wherein the 1.5% weight % of volatile oligomers is adjusted to by thorough heating, whereby to result in dimensional stability of the impression, wherein said composition undergoes a linear shrinkage of 0.20% or less after 24 hours at 23° C. according to ADA Specification No. 19.

2. A composition according to claim 1, wherein the maximum content of the volatile oligomers is about 0-0.8% by weight.

3. A dental impression produced by molding a composition according to claim 1.

4. A composition according to claim 1, wherein the composition further comprises a colorant.

5. In a method for applying a dental impression comprising contacting a dental impression material with a toothed, partially toothed or toothless jaw, the improvement comprising the impression material being a composition according to claim 1.

6. A silicone impression material according to claim 1, wherein the catalyst is a platinum complex prepared from hexachloroplatinic (IV) acid.

7. A silicone impression material according to claim 1, wherein the filler is selected from the group consisting of ground quartz flors, cristabalite flors, calcium sulphate, calcium carbonate, diatomaceous earth, precipitated silicon dioxide and pyrogenically prepared silicon dioxide.

* * * * *